(12) United States Patent
Marbet et al.

(10) Patent No.: US 11,890,408 B2
(45) Date of Patent: Feb. 6, 2024

(54) MEDICAL SUCTION PUMP

(71) Applicant: MEDELA HOLDING AG, Baar (CH)

(72) Inventors: Regina Marbet, Rütschelen (CH); Marcel Muther, Ebikon (CH); Daniela Käppeli, Zug (CH); Andreas Walter, Uster (CH)

(73) Assignee: MEDELA HOLDING AG, Baar (CH)

( * ) Notice: Subject to any disclaimer, the term of this patent is extended or adjusted under 35 U.S.C. 154(b) by 135 days.

(21) Appl. No.: 16/762,782

(22) PCT Filed: Nov. 9, 2018

(86) PCT No.: PCT/EP2018/080799
§ 371 (c)(1),
(2) Date: May 8, 2020

(87) PCT Pub. No.: WO2019/096700
PCT Pub. Date: May 23, 2019

(65) Prior Publication Data
US 2020/0300237 A1 Sep. 24, 2020

(30) Foreign Application Priority Data
Nov. 14, 2017 (EP) .................................. 17201540

(51) Int. Cl.
*A61M 1/00* (2006.01)
*F04B 45/047* (2006.01)
(Continued)

(52) U.S. Cl.
CPC ................ *A61M 1/90* (2021.05); *A61M 1/06* (2013.01); *A61M 1/65* (2021.05); *A61M 1/80* (2021.05);
(Continued)

(58) Field of Classification Search
CPC ...... F04B 17/03; F04B 17/06; F04B 39/0044; F04B 45/047; F04B 53/001–004;
(Continued)

(56) References Cited

U.S. PATENT DOCUMENTS 4,806,083 A * 2/1989 LaGrange ............... F04B 53/00
264/272.2
4,950,133 A * 8/1990 Sargent ................. F04D 29/664
4/541.5
(Continued)

FOREIGN PATENT DOCUMENTS

WO WO-2006/032156 A1 3/2006
WO WO-2009/047524 A2 4/2009
(Continued)

OTHER PUBLICATIONS

International Search Report for Application No. PCT/EP2018/080799, dated Jun. 13, 2019.

*Primary Examiner* — Alexander B Comley
(74) *Attorney, Agent, or Firm* — MARSHALL, GERSTEIN & BORUN LLP

(57) ABSTRACT

A motorized medical suction pump has a pump assembly for generating an underpressure, a pump assembly carrier for supporting the pump assembly, and a seat for receiving an energy accumulator. The pump assembly arranged in the pump assembly carrier defines a first longitudinal axis, and the seat defines a second longitudinal axis. The pump assembly carrier forms the seat. The second longitudinal axis extends at an angle to the first longitudinal axis. This suction pump is small and compact and has good sound damping.

10 Claims, 6 Drawing Sheets

(51) Int. Cl.
 *F04B 53/00* (2006.01)
 *F04B 53/16* (2006.01)
 *A61M 1/06* (2006.01)
(52) U.S. Cl.
 CPC .......... *F04B 45/047* (2013.01); *F04B 53/001* (2013.01); *F04B 53/16* (2013.01)
(58) Field of Classification Search
 CPC ............ A61M 1/06; A61M 1/65; A61M 1/80; A61M 1/90
 USPC ........................................................ 417/363
 See application file for complete search history.

(56) References Cited

U.S. PATENT DOCUMENTS

| | | | | | |
|---|---|---|---|---|---|
| 5,145,335 | A | * | 9/1992 | Abelen | F04B 39/066 417/410.3 |
| 6,155,801 | A | * | 12/2000 | Elnar | A61H 33/028 417/363 |
| 7,617,823 | B2 | * | 11/2009 | DiMatteo | A61M 16/0066 128/204.18 |
| 8,727,748 | B2 | * | 5/2014 | Groeger | F04B 53/08 417/371 |
| 2002/0002906 | A1 | * | 1/2002 | Fuesser | F04D 29/664 96/381 |
| 2005/0287007 | A1 | * | 12/2005 | Leonhard | F04B 53/003 417/11 |
| 2011/0017544 | A1 | * | 1/2011 | Bodwell | F04B 35/06 181/200 |
| 2014/0158131 | A1 | * | 6/2014 | Kenyon | F04D 29/5806 128/204.18 |
| 2015/0025482 | A1 | * | 1/2015 | Begin | A61M 1/0001 604/318 |
| 2015/0027561 | A1 | * | 1/2015 | Mauthe | A61C 17/065 137/377 |
| 2017/0368239 | A1 | * | 12/2017 | Askem | A61M 1/73 |
| 2018/0333523 | A1 | * | 11/2018 | Chang | A61M 1/74 |

FOREIGN PATENT DOCUMENTS

| | | | | |
|---|---|---|---|---|
| WO | WO-2015/109934 A1 | | 7/2015 | |
| WO | WO-2015109934 A1 | * | 7/2015 | ............... A61M 1/06 |
| WO | WO-2016/103031 A1 | | 6/2016 | |
| WO | WO-2016103031 A1 | * | 6/2016 | .......... A61M 1/0086 |
| WO | WO-2017/139437 A1 | | 8/2017 | |
| WO | WO-2017/140562 A1 | | 8/2017 | |
| WO | WO-2017/157691 A1 | | 9/2017 | |

* cited by examiner

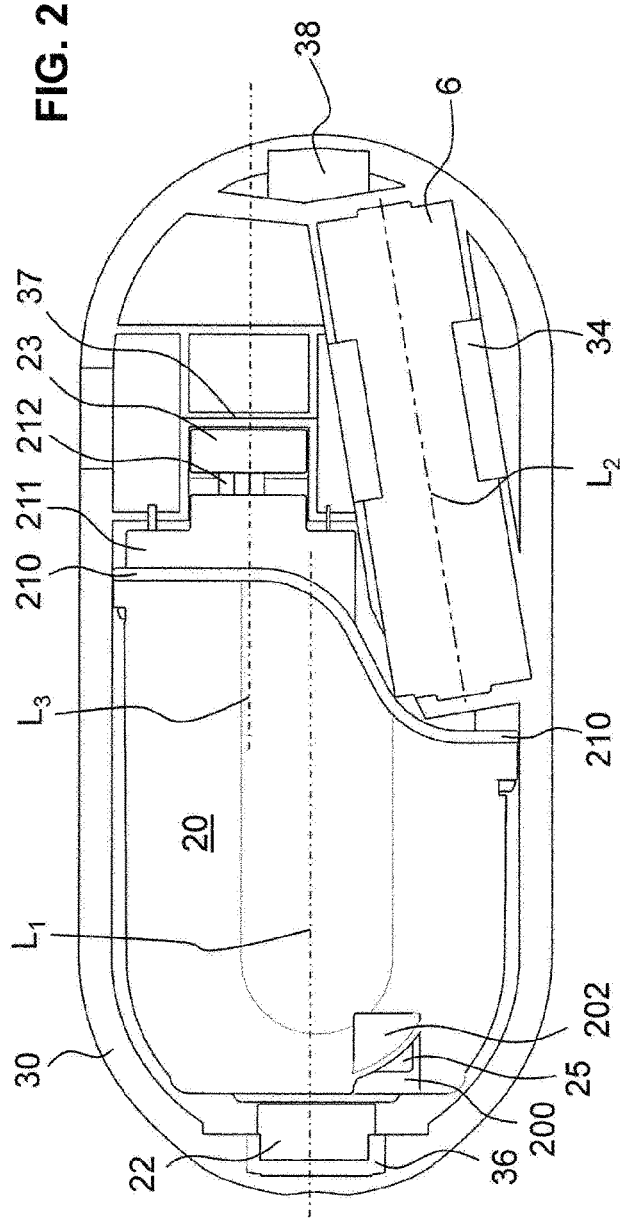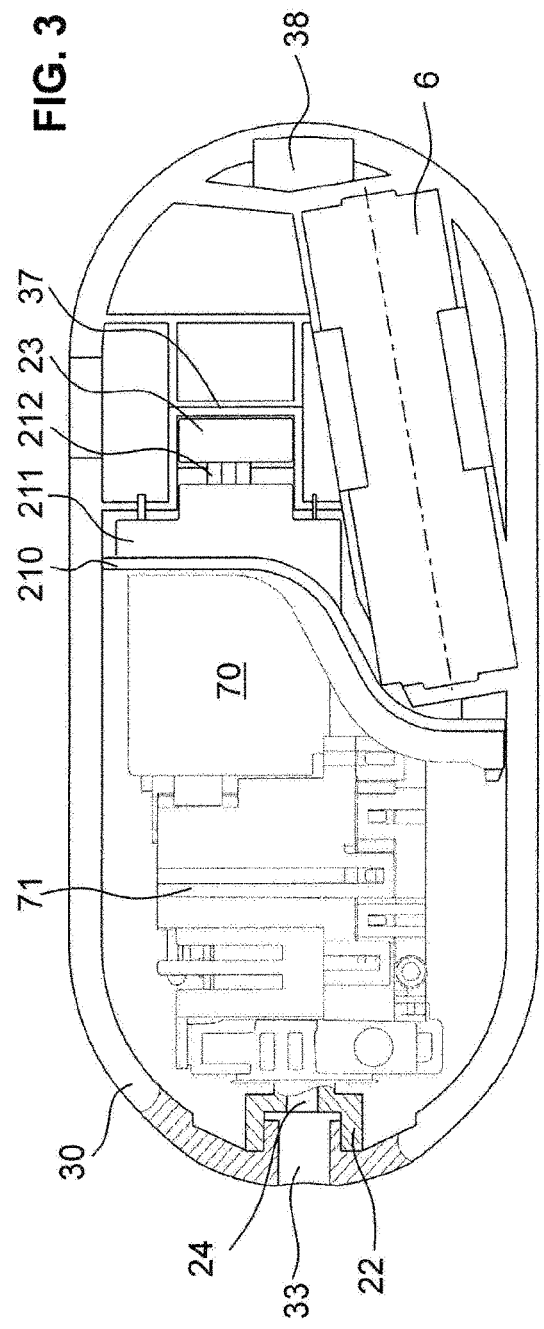

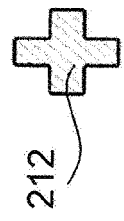
FIG. 12a
FIG. 12b
FIG. 12c
FIG. 12d
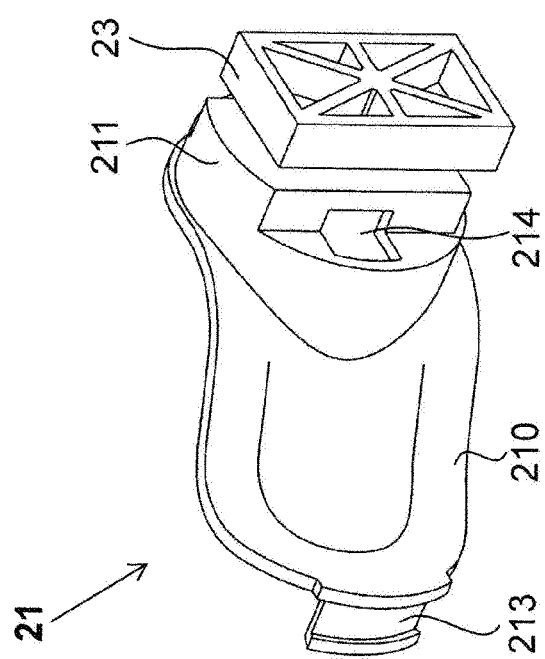
FIG. 10
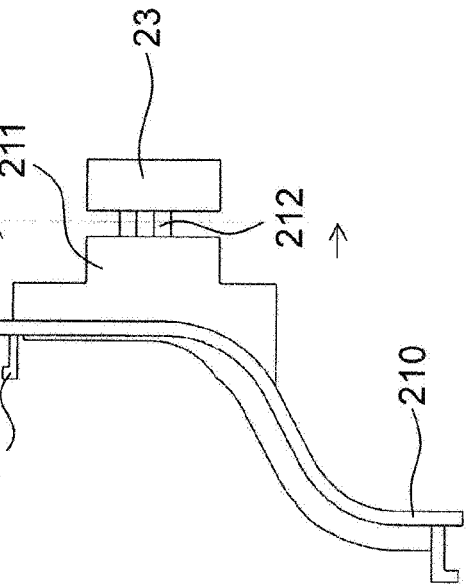
FIG. 11

MEDICAL SUCTION PUMP

CROSS-REFERENCE TO RELATED APPLICATION

The present application is the US national phase of International Patent Application No. PCT/EP2018/080799, filed Nov. 9, 2018, which claims priority to European Application No. 17201540.6, filed Nov. 14, 2017. The priority application, EP 17201540.6, is hereby incorporated by reference in its entirety.

TECHNICAL FIELD

The present invention relates to a medical suction pump, in particular a motorized medical suction pump. Suction pumps of this kind are in particular breast pumps for expressing human breastmilk or drainage pumps for aspirating body liquids, for example for chest drainage or for wound drainage.

PRIOR ART

Medical suction pumps, also called vacuum pumps, are known for a wide variety of uses. For example, they are used as breast pumps for expressing human breastmilk or as drainage pumps for aspirating body liquids. Such suction pumps have piston pumps or diaphragm pumps as a pump assembly. The use of a pump diaphragm has the advantage that the suction pump as a whole can be made relatively small and light and therefore portable during use. A motorized pump assembly that is very small but nevertheless satisfies the strict demands placed on a breast pump is disclosed in WO 2006/032156 A1. Portable suction pumps usually also have an energy accumulator for operating a motor of the pump assembly. The size of the energy accumulator and the size of the pump assembly thus substantially determine the size of the pump housing.

A further requirement of such suction pumps concerns sound damping. The pump assembly is often quite noisy, and rhythmically recurring noises disturb the user. It is therefore known to embed the pump assembly in a sound-attenuating or sound-damping environment. In this text, sound attenuating and sound damping are treated as equal and are each designated as sound-damping.

WO 2017/157691 A1 discloses a medical suction pump with an elastic bearing of the pump assembly inside a pump housing.

The pump assembly in WO 2015/109934 A1 is arranged in a closed inner housing, and a battery is arranged, parallel to the inner housing, in an outer pump housing.

The pump assembly in WO 2017/140562 A1 is secured in an outer pump housing by means of springs.

DISCLOSURE OF THE INVENTION

It is therefore an object of the invention to make available a medical suction pump which, while being as compact as possible, is also robust.

The motorized medical suction pump according to the invention has a pump assembly for generating an underpressure, a pump assembly carrier for supporting the pump assembly, and a seat for receiving an energy accumulator, wherein the pump assembly arranged in the pump assembly carrier defines a first longitudinal axis and the seat defines a second longitudinal axis. According to the invention, the pump assembly carrier forms the seat, and the second longitudinal axis extends at an angle to the first longitudinal axis.

By means of the pump assembly carrier forming the seat for the energy accumulator, and by virtue of the angled arrangement of pump assembly and energy accumulator, there are practically no empty spaces present, and the size of the suction pump as a whole is minimized. Since pump assembly and energy accumulator are held by the same pump assembly carrier, the device as a whole is relatively stiff. This not only increases the robustness of the device, it also minimizes vibrations during the operation of the pump assembly and thus reduces the generation and transmission of noise.

In preferred embodiments, the pump assembly carrier is designed substantially as a frame. The frame can have any desired shape. However, it preferably has a substantially elongate, rounded basic shape, in particular an elliptic or oval basic shape. The design as a frame permits a lightweight structure and additionally increases the stiffness. Moreover, a minimum of material is needed, which correspondingly reduces the production costs. The frame is preferably formed in one piece. It is preferably produced by plastic injection moulding.

Preferably, the suction pump comprises a first pump housing part and a second pump housing part, wherein the pump assembly carrier is held between the first pump housing part and the second pump housing part. It is thus fixed in its position, and its stiffness is increased.

In preferred embodiments, the pump assembly carrier forms a part of the pump housing. It preferably forms a connection part, visible from the outside, between the first pump housing part and the second pump housing part. This makes assembling the individual components easier, and a further bearing of the pump assembly carrier inside the pump housing can thereby be avoided.

The entire pump assembly carrier is preferably formed in one piece.

In preferred embodiments, at least two elastic bearings are present for supporting the pump assembly in the pump assembly carrier. In this way, it is possible to minimize or avoid the transmission of vibrations and structure-borne sound from the pump assembly to the pump assembly carrier and thus to the pump housing. Moreover, the pump assembly is thus held in a defined position and yet suspended flexibly, such that the noise development is reduced and/or damped. A two-point support is preferably present. However, it is also possible to use a three-point or multi-point support. The bearings are preferably formed from an elastomer.

Preferably, at least a first of these bearings forms a vacuum port. At least a second of these bearings, which preferably forms the counterbearing to the first bearing, is preferably arranged at a motor-side end of the pump assembly and in a continuation of a motor shaft of the pump assembly, i.e. in the alignment of the motor shaft.

Preferably, exactly two bearings are present, which are arranged at opposite ends of the pump assembly along the first longitudinal axis. These two bearings are preferably mutually offset with respect to the first longitudinal axis. The use of exactly two elastic bearings and/or said arrangement of the bearings minimizes the size of the suction pump as a whole and additionally has the effect that vibrations and structure-borne sound can only propagate to a limited extent, if at all.

The sound damping is optimized if the pump assembly is arranged in a sound-damping housing, and the sound-damping housing is held in the pump assembly carrier.

Preferably, an air inlet opening is present which is covered by a sound-damping element. The air inlet opening is preferably arranged in the sound-damping housing, which minimizes hissing noises when the ambient air is sucked in. The sound-damping element is preferably made of foam or of another suitable porous or air-permeable material. The pump housing is preferably made untight in a known manner, such that an air exchange from the interior of the pump housing to the environment and vice versa can take place at several places.

Preferably, the sound-damping housing has a case with a receiving opening for receiving the pump assembly, and a lid for closing the case, wherein the lid has a curved shape. This makes assembling the device easier and allows the sound-damping housing to be designed to take up as little space as possible. The case is preferably made of a stiff or semi-stiff material, in particular a plastic, and the lid is preferably made of a soft material.

Preferably, the sound-damping housing is supported in the pump assembly carrier by means of the at least two elastic bearings. Preferably, the at least two elastic bearings on the one hand support the sound-damping housing in the pump housing and on the other hand support the pump assembly inside the sound-damping housing. That is to say, the same bearings have dual functions, with each bearing preferably having corresponding surfaces or formations on two opposite sides. The number of bearings required is thus reduced. The bearing arrangement is precisely defined and optimized. Moreover, its requires little space and a minimum of component parts. The sound damping is improved, assembly is made easier and the production costs are minimized.

Preferably, the first bearing is a bearing module in the form of an elastic insert element, which is held in the sound-damping housing and passes through the latter. The entire insert element is preferably soft and produced in one piece, for example from silicone or TPE (thermoplastic elastomer). The insert element serves as a two-sided bearing and additionally closes the sound-damping housing.

Preferably, the second bearing is lid or a bearing module in the form of part of a lid of the sound-damping housing, wherein the entire lid is elastic. It is preferably made of a soft material, e.g. silicone or TPE. The stiffness of the bearing point can be defined by the chosen shape of the lid. The lid itself can form the second bearing or can form at least parts of this bearing.

Individual elements can also be combined, even without the angled arrangement of pump assembly and energy accumulator or without the arrangement of these two components on a common pump assembly carrier, in order to form other suction pumps according to the invention. Examples of these are given below and are likewise claimed as separate inventions. The preferred embodiments mentioned above, in particular the features of the dependent patent claims, can also be correspondingly combined with these examples without using all the features of Patent Claim 1.

In a preferred embodiment likewise claimed as an invention, a medical suction pump has a pump housing, a pump assembly arranged in the pump housing for the purpose of generating an underpressure, and at least a first elastic bearing and a second elastic bearing for supporting the pump assembly in the pump housing. The first elastic bearing is located at a first end of the pump assembly, and the second elastic bearing is located at a second end of the pump assembly opposite the first end. The first elastic bearing forms a vacuum port. This arrangement takes up very little space and optimally reduces vibrations.

In another embodiment likewise claimed as an invention, a medical suction pump has a pump assembly, a sound-damping housing for receiving the pump assembly, and a pump housing for receiving the sound-damping housing. The sound-damping housing has a case for receiving the pump assembly, and a lid for closing the case. The lid is elastic and has an elastic bearing for supporting the sound-damping housing in the pump housing. This design makes assembling the device easy, since the pump assembly simply has to be pushed into the case. The elastic and in particular soft lid optimally prevents vibrations and the propagation of structure-borne sound.

In preferred embodiments, these two variants are combined with each other. That is to say, the first bearing forms the vacuum port and the second bearing forms the lid.

In a further preferred embodiment, which is likewise claimed as a separate invention, a medical suction pump has a pump assembly, a sound-damping housing for receiving the pump assembly, and a pump housing for receiving the sound-damping housing. At least a first elastic bearing and second elastic bearing are present, wherein at least one of these two elastic bearings on the one hand supports the sound-damping housing in the pump housing and on the other hand supports the pump assembly inside the sound-damping housing. Preferably, both elastic bearings support the sound-damping housing with respect to the pump housing and also the pump assembly with respect to the sound-damping housing. That is to say, both elastic bearings are preferably designed as modules which form bearing points at two opposite sides. As has already been mentioned above, the bearing arrangement and the sound damping are optimized here, and an extremely compact structure is permitted. This embodiment can be achieved, for example, if the lid and/or the vacuum port are designed as bearings and are in each case soft and flexible at the corresponding points or overall.

Further embodiments are set forth in the dependent claims.

BRIEF DESCRIPTION OF THE DRAWINGS

Preferred embodiments of the invention are described below with reference to the drawings, which serve only for explanatory purposes and are not to be interpreted as limiting the invention. In the drawings:

FIG. 2 shows a first cross section through the suction pump according to FIG. 1;

FIG. 3 shows a second cross section through the suction pump according to FIG. 1;

FIG. 10 shows a perspective view of a second bearing module of the suction pump according to FIG. 1;

FIG. 11 shows a top view of the second bearing module according to FIG. 10;

FIG. 12a shows a cross section through an attachment opening of the second bearing module according to FIG. 11 in a first variant;

FIG. 12b shows a cross section through an attachment opening of the second bearing module according to FIG. 11 in a second variant;

FIG. 12c shows a cross section through an attachment opening of the second bearing module according to FIG. 11 in a third variant;

FIG. 12d shows a cross section through an attachment opening of the second bearing module according to FIG. 11 in a fourth variant.

DESCRIPTION OF PREFERRED EMBODIMENTS

Figure 1:
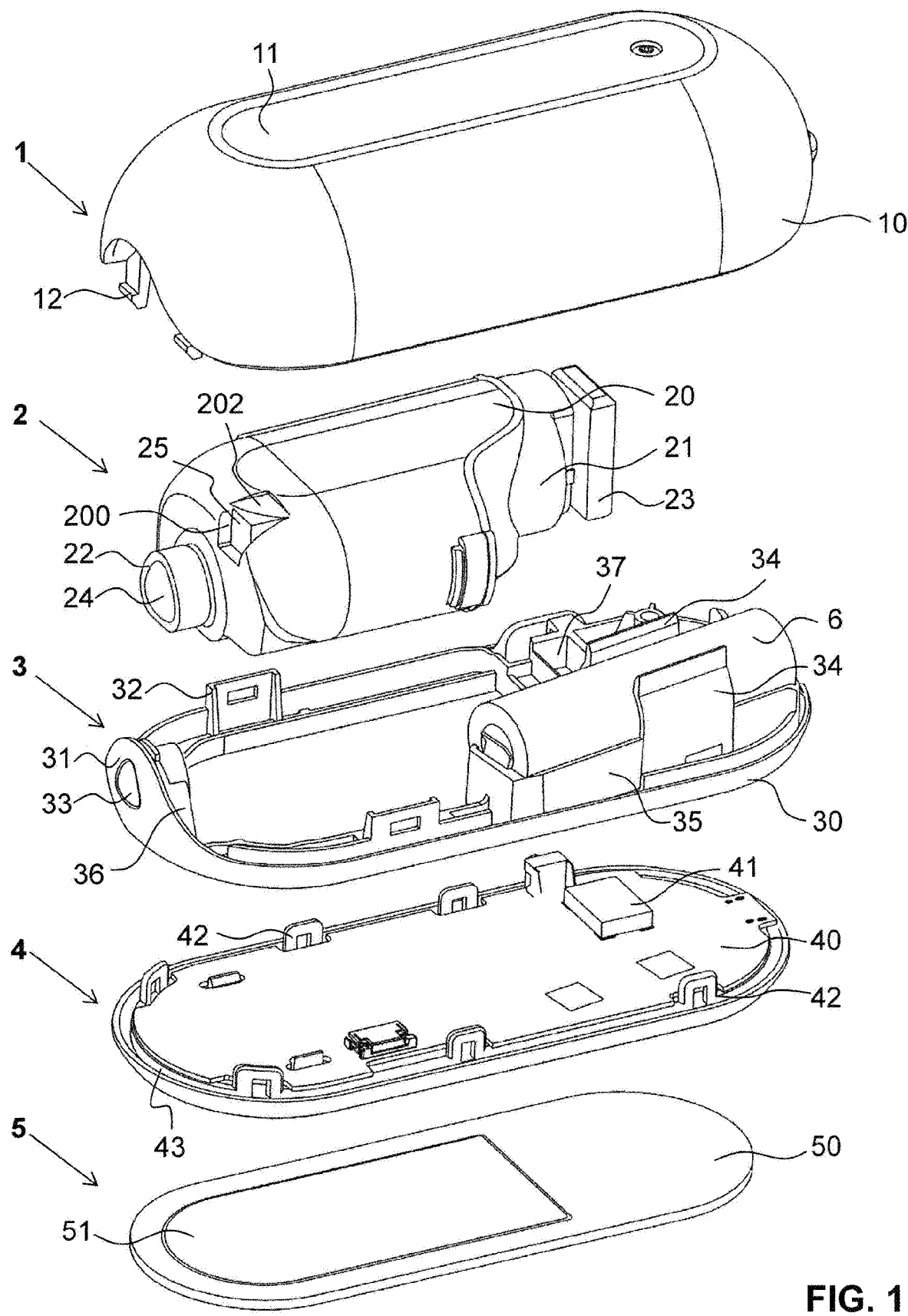
FIG. 1 shows an exploded view of a suction pump according to the invention in a first embodiment.

FIG. 1 shows a preferred illustrative embodiment of a suction pump according to the invention. It is a breast pump for expressing human breastmilk.

The suction pump has a first pump housing part 1, a sound-damping housing 2, a pump assembly carrier 3, a second pump housing part 4, and a cover 5. In the assembled state of the suction pump, the sound-damping housing 2 is located inside a pump housing, which is formed substantially by the first pump housing part 1, the second pump housing part 4, and the pump assembly carrier 3 arranged and clamped between these two parts 1, 4. The pump assembly carrier 3 is therefore preferably visible from the outside as a circumferential strip.

The first pump housing part 1 forms the bottom of the suction pump. It has a shell-shaped base body 10, of which the underside (facing upwards here) is almost flat and forms a support surface 11. The base body 10 is oval in longitudinal section. First connection elements 12, preferably snap-fit elements or other known connection means, are distributed at the circumference of the base body 10.

The second pump housing part 4 has a substantially oval base plate 40 and a peripheral channel 43 for receiving the pump assembly carrier 3. The electronic components customarily present in suction pumps are arranged on the base plate 40. They are only indicated schematically here. A control and electronics unit is designated by reference sign 41. Second connection elements 42, which engage in the frame 30, are distributed about the circumference of the second pump housing part 4.

The cover 5 forms, together with the second pump housing part 4, the upper part of the pump housing, even though these components are arranged at the bottom in this view. The cover 5 can be secured on the second pump housing part 4. It preferably has a plane-parallel, stiff and oval cover plate 50 with a display/operation window 51. By means of the display/operation window 51, it is possible, for example, to input user data and to visually present the operating mode of the suction pump.

The pump assembly carrier 3 is preferably stiff or semi-stiff. It is preferably made of a plastic and is preferably in one piece. It has an oval frame 30. At a narrow end face, the frame 30 transitions into an elevated end wall 31, which has a through-opening 33. The rear face of the end wall 31 is provided with a first bearing seat 36, which surrounds the through-opening 33. Third connection elements 32 are distributed about the circumference of the frame 30 and engage in the first pump housing part 1 in order to hold the pump housing together.

An energy accumulator seat 35 is arranged at the end of the frame 30 opposite the through-opening 33. It is configured according to the shape of an energy accumulator 6. In this example, the energy accumulator 6 is a cylindrical rechargeable battery. Other shapes and types of energy accumulators can also be used. The energy accumulator seat 35 is configured as a box that is open to the top in FIG. 1, with respective clip elements 34 protruding upwards on two opposite sides. All of these elements are preferably formed jointly in one piece with the frame 30.

A second bearing seat 37 is formed adjacent to the energy accumulator seat 35. In this example, this second bearing seat 37 is also configured as a rectangular, upwardly open box that is formed integrally on the frame 30. The rear end of the frame 30 opposite the through-opening 33 is configured as a power supply connection 38. This can be seen clearly in FIGS. 2 and 3.

The sound-damping housing 2 has a case 20 for receiving a pump assembly 7. The case 20 is preferably stiff or semi-stiff and is in particular made of plastic. It preferably has an oval, rounded shape matching the shape of the pump housing, wherein the case 20 is bevelled in the region of its opening. The bevel is preferably curved, such that the case is step-shaped and longer on one side than on the other side. This can be seen clearly in FIG. 1.

This step-shaped edge is closed by means of a lid 21. The lid 21 has a correspondingly curved closure body 210. The latter transitions preferably in one piece into an approximately cylindrical transition region 211. The diameter of this transition region 211 preferably corresponds approximately to the diameter of the longer region of the case 20. The transition region 211 is followed by a connection pin 212, which is adjoined by a second bearing module 23. This can be seen clearly in FIGS. 2 and 3. A first bearing module 22 is located at the opposite end of the case 20 and is described in more detail further below in the text.

The second bearing module 23 can be plugged onto the connection pin 212. However, it is preferably formed integrally with the latter and with the rest of the whole lid 21. The lid 21 is preferably formed elastically with the second bearing 23. It is soft in particular. It is preferably made of an elastomer or of silicone.

In the region of the first bearing module 22, the case 20 has a recess 200, which has a window 202 in the upper region. A sound-damping element 25, here a foam cube, is arranged in this recess 200.

The arrangement of the sound-damping housing 2 and of the energy accumulator 6 inside the frame 30 of the pump assembly carrier 3 can be seen clearly in FIG. 2. The sound-damping housing 2, more precisely the case 20, is supported in the first bearing seat 36 by means of the first bearing module 22. The second bearing module 23 is located in the second bearing seat 37 of the pump assembly carrier 3, such that the sound-damping housing 2 is also supported in the pump assembly carrier 3 at this opposite end. A two-point bearing is therefore present.

A through-opening of the first bearing module 22, which here forms a vacuum port 24, is in alignment with the through-opening 33 of the pump assembly carrier 3, as can be seen clearly in FIG. 3. This through-opening 33 thus forms a seat for a plug of a suction hose, which leads to a breast shield for placing on the mother's breast. Plug, suction hose and breast shield are not shown here. However, they are well known from the prior art.

As can be seen from FIG. 2, the case 20 defines a first longitudinal axis $L_1$, which is aligned with the longitudinal centre axis of the vacuum port 24. The energy accumulator 6 defines a second longitudinal axis $L_2$, which extends at an angle to this first longitudinal axis $L_1$. The second bearing module 23 defines, with its longitudinal centre axis, a third longitudinal axis $L_3$, which is parallel and offset with respect to the first longitudinal axis $L_1$.

As can be seen clearly in FIGS. 2 and 3, the available room inside the pump assembly carrier is optimally utilized by virtue of the bevelling of the case 20 and by the oblique arrangement of the energy accumulator 6, and empty spaces are largely avoided. The pump housing overall can be made very small and compact. It is sound-damped and yet stiff and robust.

The arrangement of the pump assembly 7 inside the sound-damping housing 2 is shown in FIG. 3. An exploded view matching this is found in FIG. 4.

Preferably, the pump assembly 7 corresponds substantially to the pump assembly described in WO 2006/032156 A1. However, other forms and designs can be used in the device according to the invention. The pump assembly, however, preferably comprises an electric motor and a pump unit, in particular a diaphragm pump, preferably a pump chamber with a pump diaphragm.

In the figures, the electric motor is designated by reference sign 70 and the pump unit by reference sign 71. The third longitudinal axis $L_3$ of the second bearing module 23 forms the alignment of a motor shaft (not shown) of the electric motor 70. The electric motor 70 is thus arranged adjacent to the second bearing module 23.

The pump unit 71 has a vent 710, a vacuum opening 711 and a ventilation opening 712. This can be seen clearly in FIG. 3.

Figure 6:
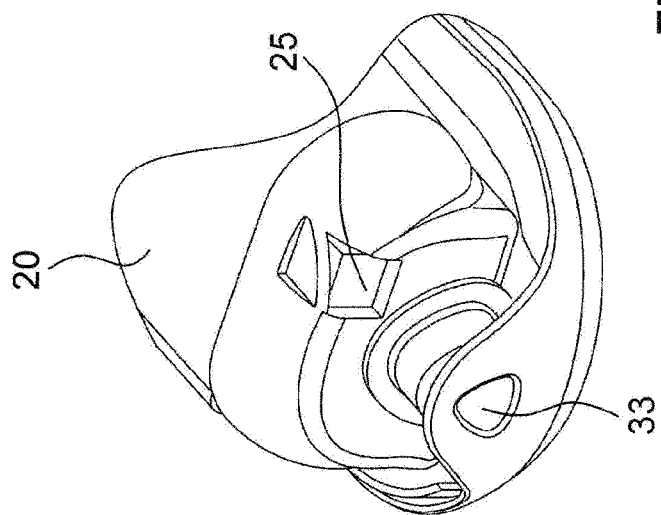
FIG. 6 shows a perspective view of a part of the suction pump according to FIG. 1 with sound-damping element.
Figure 5:
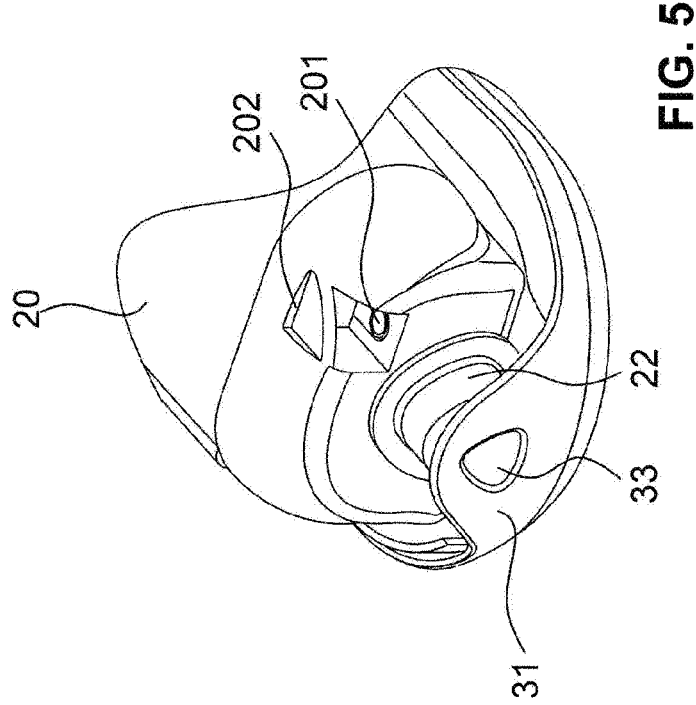
FIG. 5 shows a perspective view of a part of the suction pump according to FIG. 1 without sound-damping element.

In the assembled state of the device, the ventilation opening 712 is adjacent to an air inlet opening 201, which is located in the recess of the sound-damping housing 2. This air inlet opening 201 can be seen clearly in FIG. 5. It is covered by the sound-damping element 25, as is shown in FIG. 6. For reasons relating to injection moulding, a window 202 is present in the case 20.

The vent 710 leads into the interior of the sound-damping housing 2, more precisely of the case 20. Air, which escapes from the pump unit 71 via this vent 710, leaves the sound-damping housing 2 via leakage points, for example via a receiving element 26 of a plug connection to a plug-in element 213 of the lid 21.

Figure 4:
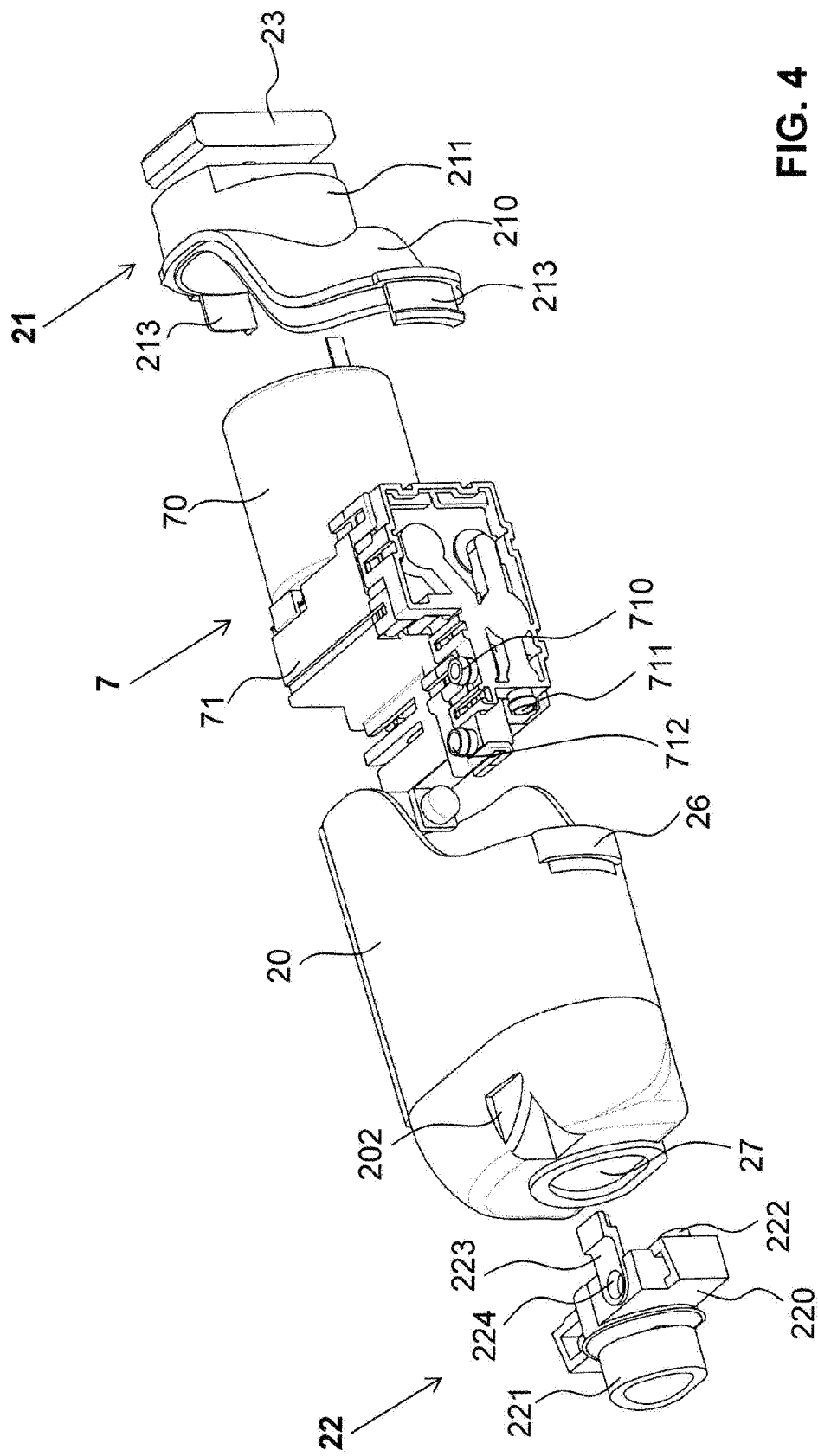
FIG. 4 shows an exploded view of a sound-damping housing with a pump assembly of the suction pump according to FIG. 1.
Figure 7:
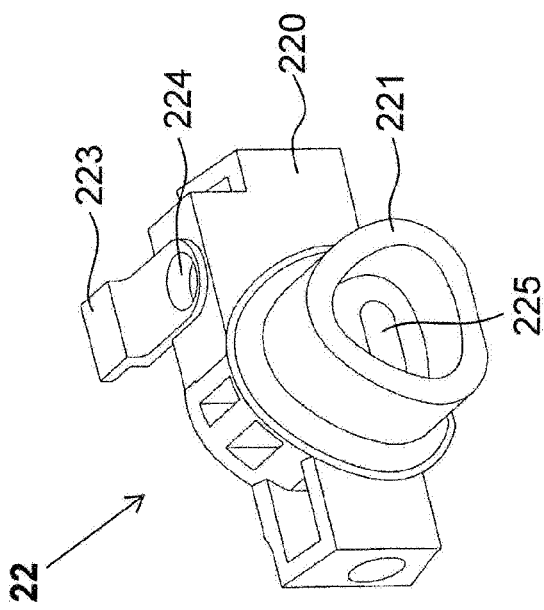
FIG. 7 shows a perspective view of a first bearing module of the suction pump according to FIG. 1.

The vacuum opening 711 is aligned with a connection channel 222 of the first bearing module 22, as can be seen in FIG. 4. In the interior of the first bearing module 22, the connection channel 222 has an angled profile, i.e. a non-rectilinear profile, and terminates in the vacuum port 24, more precisely in the attachment opening 225 present in the latter. This attachment opening 225 can be seen clearly in FIG. 7.

The pump assembly 7 is supported in the sound-damping housing 2 at the vacuum side by means of the first bearing module 22 and is supported in the sound-damping housing 2 at the motor side by means of the second bearing module 23, more precisely the lid 21. For this purpose, the lid 21 simply has to be plugged onto the case 20 and plugged with the aforementioned plug-in elements 213 into the corresponding receiving elements 26.

Figure 8:
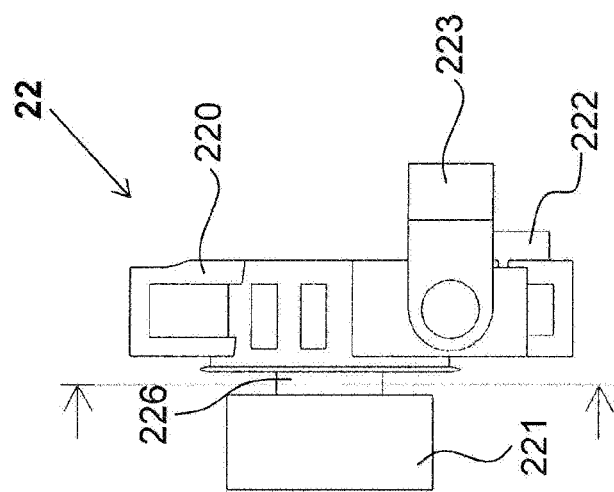
FIG. 8 shows a top view of the first bearing module according to FIG. 7.

The first bearing module 22 is not, as shown in FIG. 4, located in front of the case 20 but instead located inside the case 20. For this purpose, it can simply be pushed in via the curved opening and pushed partially through a through-opening 27 at the end face of the case 20. An attachment body 221 protrudes from the opening, a neck 226 stands free, and a base body 220 seals off the interior of the case 20 on the inner face thereof. These parts can be seen clearly in FIGS. 7 and 8. A clamp element 223 in the form of a resilient tongue is preferably used to secure the base body 220 in the case 20. This tongue 223 likewise seals off the interior of the case 20.

The base body 220 has a ventilation channel 224 which creates the connection between the ventilation opening 712 of the pump unit 71 and the air inlet opening 201 of the case 20.

The entire first bearing module 22 is formed in one piece and is preferably elastic, in particular soft. It thus forms bearing points at two opposite sides: at a first side between the sound-damping housing 2 and the pump assembly carrier 3 and thus the pump housing, and at an opposite side between the sound-damping housing 2 and the pump assembly 7, more precisely the pump unit 71.

The lid too is formed in one piece with the second bearing module 23 and is preferably elastic, in particular soft. It thus also forms bearing points at two opposite sides: at a first side between the sound-damping housing 2 and the pump assembly carrier 3 and thus the pump housing, and at an opposite side between the sound-damping housing 2 and the pump assembly 7, more precisely the electric motor 70. Since the pump assembly carrier 3 is part of the outer pump housing, a further bearing is not needed.

Figure 9A:
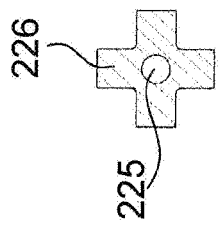
FIG. 9a shows a cross section through an attachment opening of the first bearing module according to FIG. 7 in a first variant.
Figure 9B:
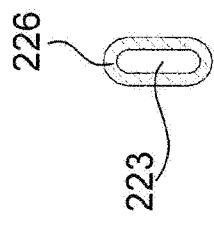
FIG. 9b shows a cross section through an attachment opening of the first bearing module according to FIG. 7 in a second variant.
Figure 9C:
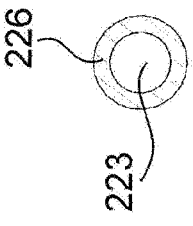
FIG. 9c shows a cross section through an attachment opening of the first bearing module according to FIG. 7 in a third variant.

The sound damping or the vibration damping can be further optimized by suitable choice of the attachment opening 225. Shapes of the kind shown in FIGS. 9a to 9c have proven useful. The neck 226 of the first bearing module 22 is shown in cross section, and also the attachment opening 225 located therein. The cross sections of the neck 226 and the shapes of the attachment opening 225 can be combined with one another in any desired manner. In FIG. 9a, the neck 226 is cross-shaped and the attachment opening 225 is round. In FIG. 9b, the neck 226 and the attachment opening 225 are oval, and in FIG. 9c they are round. The combination according to FIG. 9b is most preferred.

FIGS. 10 to 12d show the lid 21 with the second bearing module 23. As has already been described, it has the curved closure body 210, the transition region 211, the connection pin 212 and the second bearing module 23. The second bearing module 23 preferably has a cuboid frame with connection struts extending therein. It is thus elastic and adapts optimally to its associated second bearing seat 37.

Cable feedthroughs 214 in the form of through-openings are preferably present in the transition region 211 in order to connect the electric motor 70 to the control and electronics unit 41 via the base plate 40. The plug-in elements 213 are formed integrally on the curved closure body 210.

The sound damping and the bearing arrangement can be additionally optimized through the configuration of the connection pin 212. Preferred variants are shown in FIGS. 12a to 12d. The connection pin 212 is preferably solid. It is preferably relatively stiff.

Its cross section is cross-shaped in FIG. 12a, round in FIG. 12b, rectangular in FIG. 12c and oval in FIG. 12d. It is preferably cross-shaped.

The suction pump according to the invention is small and compact and has good sound damping.

LIST OF REFERENCE SIGNS

| | |
|---|---|
| 1 | first pump housing part |
| 10 | shell-shaped base body |
| 11 | support surface |
| 12 | first connection element |
| 2 | sound-damping housing |
| 20 | case |
| 200 | recess |
| 201 | air inlet opening |
| 202 | window |
| 21 | lid |
| 210 | curved closure body |
| 211 | transition region |
| 212 | connection pin |
| 213 | plug-in element |
| 214 | cable feedthroughs |
| 22 | first bearing module |
| 220 | base body |
| 221 | attachment body |
| 222 | connection channel |
| 223 | clamp element |
| 224 | ventilation channel |
| 225 | attachment opening |
| 226 | neck |
| 23 | second bearing module |
| 24 | vacuum port |
| 25 | sound-damping element |
| 26 | receiving element |
| 27 | through-opening |
| 3 | pump assembly carrier |
| 30 | frame |
| 31 | end wall |
| 32 | third connection element |
| 33 | through-opening |
| 34 | clip element |
| 35 | energy accumulator seat |
| 36 | first bearing seat |
| 37 | second bearing seat |
| 38 | power supply connection |
| 4 | second pump housing part |
| 40 | base plate |
| 41 | control and electronics unit |
| 42 | second connection element |
| 43 | channel |
| 5 | cover |
| 50 | cover plate |
| 51 | display window/operating window |
| 6 | energy accumulator |
| 7 | pump assembly |
| 70 | electric motor |
| 71 | pump unit |
| 710 | vent |
| 711 | vacuum opening |
| 712 | ventilation opening |
| $L_1$ | first longitudinal axis |
| $L_2$ | second longitudinal axis |
| $L_3$ | third longitudinal axis |

The invention claimed is:

1. A motorized medical suction pump with a pump assembly for generating a vacuum, with a pump assembly carrier for supporting the pump assembly, and with a seat receiving an energy accumulator, wherein the pump assembly arranged in the pump assembly carrier defines a first longitudinal axis, and the seat and the energy accumulator define a second longitudinal axis, wherein the pump assembly has along the first longitudinal axis a first end and a second end, the first end and the second end being opposite ends, wherein the pump assembly carrier forms the seat, wherein the second longitudinal axis extends at an angle to the first longitudinal axis, and wherein exactly two bearings consisting of a first elastic bearing and a second elastic bearing are present for supporting the pump assembly in the pump assembly carrier, wherein the first elastic bearing is arranged at the first end of the pump assembly and the second elastic bearing is arranged at the second end of the pump assembly, wherein the pump assembly is arranged in a sound-damping housing, and the sound-damping housing is held in the pump assembly carrier, wherein the sound-damping housing is supported in the pump assembly carrier by means of the first elastic bearing and the second elastic bearing, and wherein the first elastic bearing and the second elastic bearing on the one hand support the sound-damping housing in a pump housing and on the other hand support the pump assembly inside the sound-damping housing.

2. The motorized medical suction pump according to claim 1, wherein the pump assembly carrier defines an oblong shape.

3. The motorized medical suction pump according to claim 1, wherein the pump housing comprises a first pump housing part and a second pump housing part, and wherein the pump assembly carrier is held between the first pump housing part and the second pump housing part.

4. The motorized medical suction pump according to claim 1, wherein an air inlet opening is present, which is covered by a sound-damping element.

5. The motorized medical suction pump according to claim 1, wherein the first elastic bearing forms a vacuum port, and the second elastic bearing is arranged at a motor-side end of the pump assembly and is in alignment with a motor shaft of the pump assembly.

6. The motorized medical suction pump according to claim 1, wherein the first elastic bearing and the second elastic bearing are mutually offset with respect to the first longitudinal axis.

7. The motorized medical suction pump according to claim 1, wherein the sound-damping housing has a case with a receiving opening for receiving the pump assembly, and a lid for closing the case, wherein the lid has a curved shape.

8. The motorized medical suction pump according to claim 1, wherein the first elastic bearing is an elastic insert element, which is held in the sound-damping housing and passes through the sound-damping housing.

9. The motorized medical suction pump according to claim 1, wherein the second elastic bearing of the two elastic bearings is part of a lid of the sound-damping housing, wherein the entire lid is elastic.

10. The motorized medical suction pump according to claim 1, wherein the pump assembly carrier defines a frame and has an oblong shape.

* * * * *